United States Patent
Collins et al.

(10) Patent No.: US 8,851,746 B2
(45) Date of Patent: Oct. 7, 2014

(54) GEOTHERMAL HEATING AND/OR COOLING SYSTEM GROUT TESTING

(71) Applicant: Halliburton Energy Services, Inc., Houston, TX (US)

(72) Inventors: Ryan Patrick Collins, Spring, TX (US); Shantel Stone, Conroe, TX (US); Laura Kuri, Spring, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 48 days.

(21) Appl. No.: 13/661,744

(22) Filed: Oct. 26, 2012

(65) Prior Publication Data

US 2014/0119401 A1    May 1, 2014

(51) Int. Cl.
*G01N 25/18*    (2006.01)
*C04B 24/38*    (2006.01)
*C04B 28/02*    (2006.01)

(52) U.S. Cl.
CPC .............. *G01N 25/18* (2013.01); *C04B 24/383* (2013.01); *C04B 28/02* (2013.01)
USPC ............. 374/43; 106/713; 106/719; 106/638; 374/44

(58) Field of Classification Search
CPC .......... C04B 14/06; C04B 7/00; C04B 16/04; G01N 15/02; G01N 15/08; G01N 31/22; G01N 33/24; G01N 33/483; G01N 25/18; E21B 43/38; E21B 33/13; A61B 10/00; B01D 25/00
USPC ........ 106/638, 719, 803, 713, 716; 73/15, 38, 73/61, 152.04; 166/292, 293; 324/65; 374/44
See application file for complete search history.

(56) References Cited

U.S. PATENT DOCUMENTS 3,412,325 A * 11/1968 Soderling ...................... 324/693
3,533,274 A * 10/1970 Bishop et al. ................... 374/44
5,059,319 A * 10/1991 Welsh ............................ 210/232

(Continued)

FOREIGN PATENT DOCUMENTS

EP         1955656 A1 *  8/2008
JP    2007051492 A  *  3/2007

OTHER PUBLICATIONS

Technical Data, Sand Content Kit: Sand Content Measurement Tool, Cetco®, REV. 1/11, © 2011, p. 1; http://drillingproducts.cetco.com/DesktopModules/Bring2mind/DMX/Download.aspx?EntryId=4897&Command=Core_Download&language=en-US&PortalId=13&TabId=1489.*

(Continued)

*Primary Examiner* — Lisa Caputo
*Assistant Examiner* — Gregory A Royal
(74) *Attorney, Agent, or Firm* — Anthony Iannitelli; Conley Rose, P.C.

(57) ABSTRACT

A subterranean grouting method including (a) placing a sample of a grout mixture within a test container, (b) separating a sand component from the sample, (c) determining if the grout mixture exhibits a thermal conductivity within a predetermined thermal conductivity range based upon a proportion of the sand component within the sample, and (d) upon determining that the grout mixture exhibits a thermal conductivity with the predetermined thermal conductivity range, securing a conduit within a subterranean bore with the grout mixture, wherein (a), (b), (c), and (d) are carried out proximate each other at a job site.

21 Claims, 4 Drawing Sheets

(56) References Cited

U.S. PATENT DOCUMENTS

| | | | | |
|---|---|---|---|---|
| 5,672,814 | A | * | 9/1997 | Doherty .......................... 73/38 |
| 6,251,179 | B1 | * | 6/2001 | Allan ............................ 106/719 |
| 6,502,636 | B2 | * | 1/2003 | Chatterji et al. ............. 166/293 |
| 7,067,044 | B1 | * | 6/2006 | Coon ............................ 203/10 |
| 2003/0188666 | A1 | * | 10/2003 | Johnson et al. .............. 106/638 |
| 2010/0313645 | A1 | * | 12/2010 | Doman et al. ............. 73/152.04 |
| 2014/0014341 | A1 | * | 1/2014 | Hathcox et al. ............... 166/292 |

OTHER PUBLICATIONS

Sand Contest Test, Cetco®, YouTube, uploaded Feb. 25, 2012 (snapshots of relevant disclosures), 5 pages; http://www.youtube.com/watch?v=w6IG_OrjJGs.*

Florida Method of Test for Sand Content of Slurry, Sep. 1, 2000, pp. 1 and 2; http://www.dot.state.fl.us/statematerialsoffice/administration/resources/library/publications/fstm/methods/FM8-RP13B-3.pdf.*

OFI Testing Equipment, Inc., Sand Content Kit with Case, Ofite®, Updated May 28, 2009, Ver. 1.2, © 2011; http://www.ofite.com/instructions/167-00-C.pdf.*

Khan et al., Zulfi's Formula for Analysis of Hardened Mortar, Aug. 18, 2009, 34$^{th}$ Conference on Our World in Concrete & Structures, Singapore, CI-Premier PTE LTD, 9 pages; http://www.cipremier.com/e107_files/downloads/Papers/100/34/100034020.pdf.*

Indicate—Defintion and More from the Free Merriam-Webster Dictionary, May 22, 2014, 2 pages; see http://www.merriam-webster.com/dictionary/indicate.*

Correlate—Definition and More from the Free Merriam-Webster Dictionary, May 30, 2014, 3 pages; see http://www.merriam-webster.com/dictionary/correlate.*

\* cited by examiner

GEOTHERMAL HEATING AND/OR COOLING SYSTEM GROUT TESTING

BACKGROUND

Heating and/or cooling systems are often used to heat and cool closed in structures. Occasionally, heating and/or cooling systems will utilize heat sink properties of subterranean formations to provide heating and/or cooling. These systems are referred to as geothermal heating and/or cooling systems. In some embodiments, a geothermal heating and/or cooling system may increase a structure's energy efficiency. When geothermal heating and/or cooling systems are constructed, it is common to dispose at least one coil in a bore formed within a subterranean formation. Often, it may be desirable to dispose a grout with the at least one coil in the bore, for example, so secure such a coil within the bore. When selecting and/or preparing a grout for utilization in such a setting, it may be desirable to ensure that the selected and/or prepared grout will be effective for the purposes of the geothermal heating/and or cooling system, for example, to ensure that the thermal conductivity of the grout will be sufficient so as to allow heat transfer between the coil and the subterranean formation. As such, apparatuses, systems, and methods of assessing the thermal conductivity of such a grout are needed.

SUMMARY

Disclosed herein is a subterranean grouting method comprising (a) placing a sample of a grout mixture within a test container, (b) separating a sand component from the sample, (c) determining if the grout mixture exhibits a thermal conductivity within a predetermined thermal conductivity threshold based upon a proportion of the sand component within the sample, and (d) upon determining that the grout mixture exhibits a thermal conductivity with the predetermined thermal conductivity range, securing a conduit within a subterranean bore with the grout mixture, wherein (a), (b), (c), and (d) are carried out proximate each other at a job site.

These and other features will be more clearly understood from the following detailed description taken in conjunction with the accompanying drawings and claims.

BRIEF DESCRIPTION OF THE DRAWINGS

For a more complete understanding of the present disclosure and the advantages thereof, reference is now made to the following brief description, taken in connection with the accompanying drawings and detailed description.

DETAILED DESCRIPTION OF THE EMBODIMENTS

Figure 1A:
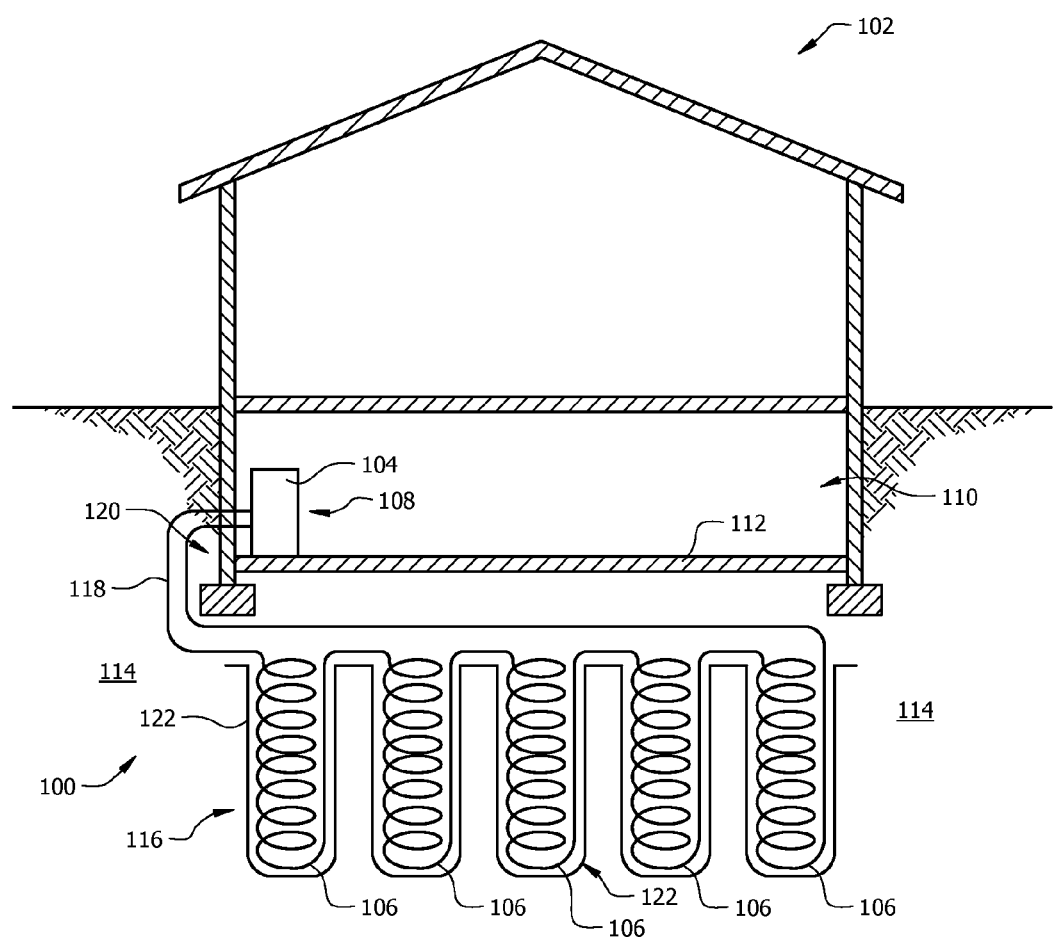
FIG. 1A is a schematic elevation view of an embodiment of a subterranean formation and geothermal heat pump system.

In the drawings and description that follow, like parts are typically marked throughout the specification and drawings with the same reference numerals, respectively. The drawing figures are not necessarily to scale. Certain features of the invention may be shown exaggerated in scale or in somewhat schematic form and some details of conventional elements may not be shown in the interest of clarity and conciseness.

Unless otherwise specified, any use of any form of the terms "connect," "engage," "couple," "attach," or any other term describing an interaction between elements is not meant to limit the interaction to direct interaction between the elements and may also include indirect interaction between the elements described. In the following discussion and in the claims, the terms "including" and "comprising" are used in an open-ended fashion, and thus should be interpreted to mean "including, but not limited to . . . ." Reference to up or down will be made for purposes of description with "up," "upper," "upward," or "above" meaning toward the surface of the bore and with "down," "lower," "downward," or "below" meaning toward the terminal end of the well, regardless of the bore orientation. The various characteristics mentioned above, as well as other features and characteristics described in more detail below, will be readily apparent to those skilled in the art with the aid of this disclosure upon reading the following detailed description of the embodiments, and by referring to the accompanying drawings.

Disclosed herein are embodiments of a method for assessing the thermal conductivity of a grout in a non-laboratory setting, for example, in the performance of a grouting operation during installation of service of a geothermal heating and/or cooling system. Also disclosed herein are embodiments of apparatuses and systems which may be utilizing in the performance of such methods, for example, to assess the thermal conductivity of a grout in a non-laboratory setting.

Figure 1B:
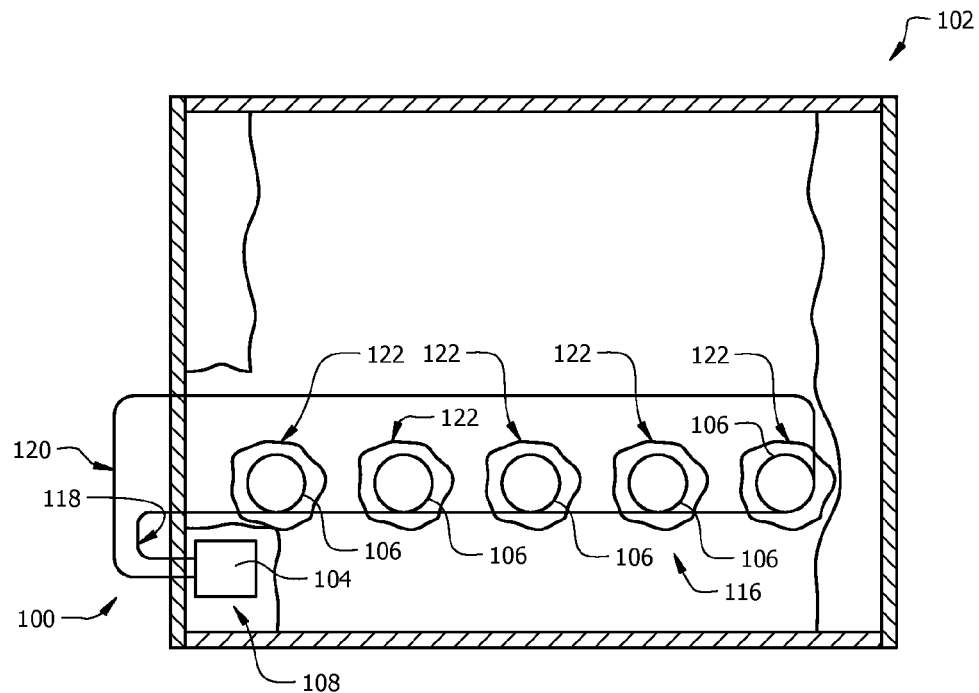
FIG. 1B is a schematic top view of an embodiment of a subterranean formation and geothermal heat pump system.

Turning now to FIGS. 1A and 1B, an embodiment in which such methods, apparatuses, and/or systems may be utilized is illustrated. In the embodiment of FIGS. 1A and 1B, a heating and/or cooling system is shown and is generally indicated by reference numeral 100. In an embodiment, the heating and/or cooling system 100 may generally comprise a geothermal heating and/or cooling system. In this example, the geothermal heating and/or cooling system 100 services a building structure 102, such as a house. Those of skill in the art will appreciate that the building structure 102 need not be residential and, in fact, can be virtually any building structure whose internal climate is desirably controlled. In an additional or alternative embodiment, the building structure 102 may comprise an external climate that needs to be controlled.

In the embodiment of FIGS. 1A and 1B, the heating and/or cooling system 100 comprises a heat exchange unit 104 and at least one coil 106 in fluid communication with the heat exchange unit 104. For example, in the embodiment of FIGS. 1A and 1B, the system comprises five coils, however, any suitable number of coils may be employed. In an embodiment, a heat exchange fluid may be circulated through the heat exchange unit 104 and the at least one coil 106. In an embodiment, the heat exchange fluid may be any suitable heat exchange medium, such as a water and ethylene glycol mixture.

In an embodiment, the at least one coil 106 may be disposed at a first location 116. In an embodiment, the first location 116 may be any location at least partially in contact with a heat sink. In an embodiment the first location 116 may be within a subterranean formation 114. In an embodiment, the first location 116 may be at a depth below a regional frost line. In an embodiment, regardless of the depth of the regional frost line, at least a portion (e.g. a substantial portion) of the at least one heat exchange pipe may be disposed within the ground at a depth of at least two feet, for example, at a depth of at least three feet, at a depth of at least four feet, at a depth of at least five feet, at a depth of at least six feet, or at any suitable depth. In an embodiment of a vertical system (e.g., as illustrated in FIGS. 1A and 1B), vertical holes or bores 124 may be drilled in the ground as deep as about 250 feet deep. Additionally or alternatively, in an embodiment, the first location 116 may be within a subterranean formation 114 directly beneath the foundation slab 112. Alternatively, in an embodiment, the first location 116 may be within a subterranean formation 114 proximate to the foundation slab 112. Alternatively, in an embodiment, the first location 116 may be disposed in a body of at least one fluid, such as water or air.

In an embodiment, the at least one coil 106 may be arranged to form a single fluid circuit so that heat exchange fluid fed into the at least one coil 106 by the heat exchange unit 104 follows a path (e.g., a serial path) through the at least one coil 106 before returning to the heat exchange unit 104. To that end, the at least one coil 106 comprises a feed conduit 118 receiving the heat exchange fluid discharged by the heat exchange unit 104, a discharge conduit 120 returning the heat exchange fluid that has circulated through the at least one coil 106 back to the heat exchange unit 104. In an embodiment, the at least one coil 106 may comprise a vertical and/or horizontal configuration. In an embodiment, the at least one coil 106 may comprise a plurality of coils in the vertical and/or horizontal configuration and/or connected in series and/or parallel. In an embodiment, the at least one coil 106 may comprise a recirculating closed circuit. In an embodiment, the at least one coil 106 may comprise an open circuit. In an embodiment, the at least one coil 106 may be comprise at least one U-turn and/or at least one loop. In an embodiment, the at least one coil 106 may be arranged in a position that is intermediate the feed conduit 118 and the discharge conduit 120.

In an embodiment, the heat exchange unit 104 may be located at a second location 108. In an embodiment, the second location 108 may be a basement 110 of the building structure 102 and, for example, rests on the foundation slab 112 of the building structure 102. Alternatively, in an embodiment, the second location 108 may be located anywhere within the building structure 102. Alternatively, in an embodiment, the second location 108 may be located outside the building structure 102. Alternatively, in an embodiment, the second location 108 may be associated with substantially anywhere heating and/or cooling is desired. Alternatively, in an embodiment, the second location 108 may be located within the subterranean formation 114. Alternatively, in an embodiment, the second location 108 may comprise multiple second locations 108 where multiple heat exchange units 104 may be disposed.

In an embodiment of a heating and/or cooling system operation, the heat exchange unit 104 delivers the heat exchange fluid to the feed conduit 118. In this embodiment, heat exchange fluid enters and passes through the feed conduit 118 and through the at least one coil 106 before being returned to the heat exchange unit 104 via the discharge conduit 120. In this embodiment, during flow of the heat exchange fluid through the at least one coil 106, heat is transferred between the subterranean formation 114 and the heat exchange fluid, through grout 122 surrounding the at least one coil 106. In this embodiment, the difference in temperature between the heat exchange fluid being fed into the at least one coil 106 by the heat exchange unit 104 and the heat exchange fluid being returned to the heat exchange unit 104 from the at least one coil 106 creates a thermal driving force that is used by the heat exchange unit 104. In this embodiment, in particular, the heat exchange unit 104 comprises a second internal loop containing a refrigerant. In this embodiment, the thermal driving force is utilized by the heat exchange unit 104 to drive the refrigerant through a vapor-compression refrigeration cycle, which in turn is used to generate heated or cooled air, as is well known to those of skill in the art. In this embodiment, this heated or cooled air is then pumped by the heat exchange unit 104 into the interior of building structure 102 to control the internal climate within the building structure 102. In an embodiment, the heat exchange fluid may be pumped through the heating and/or cooling system.

As noted above, in an embodiment, one or more conduits, illustrated as coils 106 may be secured within one or more bores 124 at the first location 116, for example, utilizing a grout 122. Although the instant disclosure may disclose methods, systems, and apparatuses for use in grouting procedures with respect to coils, such as coils 106, one of skill in the art will appreciate that various other suitable conduits may be similarly employed and, as such, the instant disclosure should not be construed as so-limited. For example, in an embodiment, grout may be utilized in holes containing power transmission lines, and heat exchange with the surrounding formation may be need to keep such lines cool and/or improve transmission efficiency. The following disclosure may be similarly applicable to any suitable downhole (e.g., underground) tubular and/or conduit which must exhibit heat-exchange with a subterranean formation.

In an embodiment, a sufficient amount of grout 122 may be disposed to secure a given coil 106 within a given bore 124. In an embodiment, for example, grout may be placed at the interface between vertically oriented coils for geothermal heat pumps and the surrounding formation, for example, to support the coils and ensure efficient heat transfer. In an embodiment, the grout 122 may provide sealing between the at least one coil 106 and a water supply (e.g., ground water). For example, a sufficient amount of grout 122 may be disposed to provide a sufficient seal between the at least one coil 106 and a water supply.

In an embodiment, the grout 122 disposed about the coils may comprise a heat transfer medium. In an embodiment, heat may be transferred between the formation 114 at the first location 116 and the heat exchange fluid through the grout 122, which may be at least partially in contact with at least one coil 106. In an embodiment, the grout 122 may be in contact with at least 50% the surface area of the at least one coil 106, alternatively, at least about 60%, alternatively, at least about 70%, alternatively, at least about 80%, alternatively, at least about 90%, alternatively, substantially a the entirety of the surface area of the coil(s) 106. In an embodiment, the grout may be in contact with a substantial portion of the surface area of the at least one coil 106. In an embodiment, the grout may be in contact with substantially all of the surface area of the at least one coil 106.

In an embodiment, the relative thermal conductivity of the grout 106 may reduce the amount of excavation required to install the at least one coil 106 in a subterranean formation 114. For example, two different grouts, a first grout and a second grout, may have different thermal conductivity coefficients, such that the first grout may more easily transfer heat between bodies than the second grout. In such an example, if a heating and/or cooling system is installed to achieve a desired heat transfer fluid temperature change from the feed conduit 118 to the discharge conduit 120, the use of the first grout acting as a heat transfer medium between at least one coil 106 and the subterranean formation 114 may require less pipe surface area and subsequently a bore with less volume, than the use of the second grout acting as the heat transfer medium to achieve the same temperature change. Thus, in this embodiment, for example, the use of the first grout requires less ground excavation to dispose a smaller coil to achieve the same temperature change.

Figure 2:
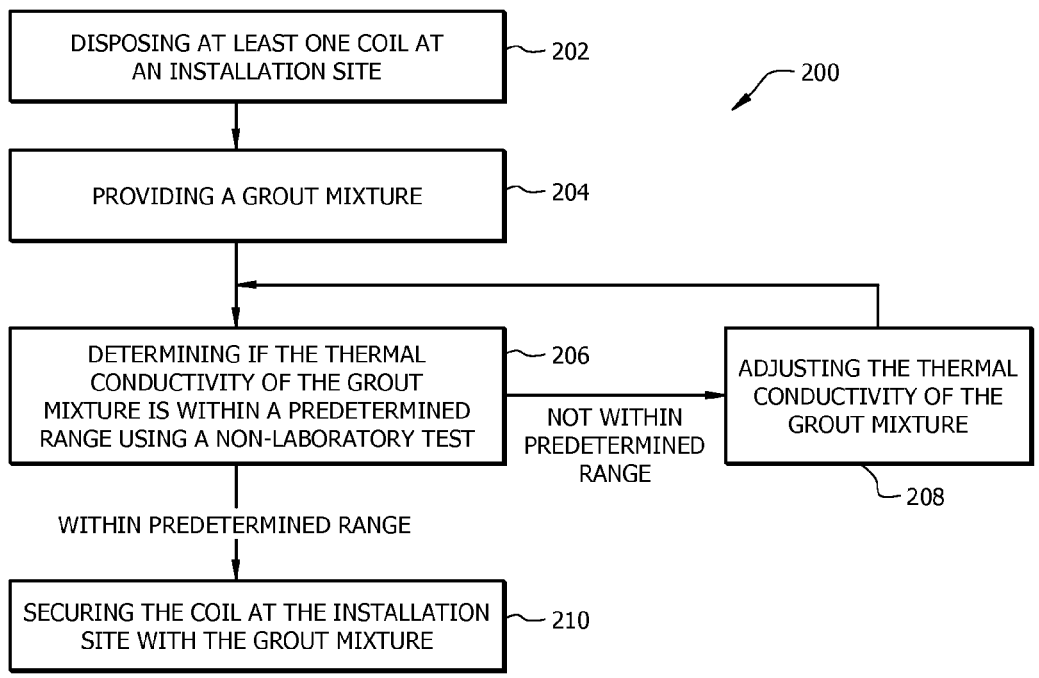
FIG. 2 is a block diagram of an embodiment of a method of grouting according to the present disclosure.

Referring to FIG. 2, an embodiment of a method for installing a heating and/or cooling system 200, for example, a geothermal system, is disclosed. In the embodiment of FIG. 2, the method for installing a geothermal system 200 generally comprises the steps of disposing at least one coil at a first location 202, providing a grout mixture 204, determining if the thermal conductivity of the grout mixture is within a predetermined range using a non-laboratory test 206, upon finding that the thermal conductivity of the grout mixture is not within the predetermined range, adjusting the thermal conductivity of the grout mixture 208, upon finding that the thermal conductivity of the grout mixture is within the predetermined range, securing the coil at the installation site with the grout mixture 210.

In an embodiment, the method comprises disposing at least one coil at a first location 202. In an embodiment, the at least one coil may be a heat exchange pipe or conduit. In an embodiment, the at least one coil may be formed of high-density polyethylene, polyvinylchloride, polypropylene, polybutylene, filled polymers, polymers and/or plastic filled with thermally conductive filler, and the like. In an embodiment, the at least one coil may comprise a metal, such as copper, aluminum, stainless steel and/or any other thermally conductive material. In an embodiment, the at least one coil may comprise an outside surface and/or inside surface with a plurality of fins. In an embodiment, the at least one coil outside surface and/or inside surface may comprise a relatively smooth surface. As previously disclosed, the at least one coil may comprise at least one loop. In an embodiment, the at least one coil may comprise a plurality of loops. In an embodiment, the at least one coil may be a plurality of coils disposed in series and/or in parallel with the heating and/or cooling system. In various embodiments, the at least one coil may be configured for horizontal and/or vertical disposition in the ground below a regional frost line, and/or submerged in water in a pond, lake, ocean, and/or river. As previous disclosed, in an embodiment, the first location may comprise a heat sink. Additionally, as previously disclosed, the position of the installation site may be relative to the position of a second location, for example, substantially proximate to where a heat exchange unit may be disposed for the purpose of operating a geothermal unit. As also disclosed herein, such installation site may comprise a bore, a tunnel, or the like. In such an embodiment, a bore or tunnel may be provided, for example, extending substantially horizontally, substantially vertically, at any suitable angle, or combinations thereof. Such a bore or tunnel may be characterized as having a suitable length, width, depth, diameter, or combinations thereof, as will be appreciated by one of skill in the art upon viewing this disclosure.

In an embodiment, the step of disposing at least one coil at a first location may comprise drilling, boring, excavating, tunneling, or otherwise providing the first location. Those of skill in the art will appreciate suitable methods, systems, and apparatuses as may be employed, upon viewing this disclose. Additionally, in an embodiment, the step of disposing at least one coil at a first location may comprise positioning such coil within the first location (e.g., within a bore, tunnel, hole, or the like). For example, one of skill in the art will appreciate various equipment (e.g., hoists, cranes, and the like) as may be suitably employed to appropriately position the coil).

In an embodiment, the method also comprises providing a grout mixture 204. In an embodiment, the step of providing a grout mixture may comprise preparing the grout mixture. In an embodiment, a suitable grout mixture may generally comprise a sand component, a clay component, a fluid component and, optionally, one or more additives. In an embodiment, the sand component may comprise at least one type of silica, for example, silica in the form of quartz. The sand may comprise particulate or granular material characterized as very fine, fine, medium, coarse, very coarse, or combinations thereof. For example, the granules may be characterized as having a size ranging from about 40 mesh to about 80 mesh, alternatively, from about 50 mesh to about 70 mesh. In an embodiment, the sand component may be present within the grout mixture in a range of from about 30% to about 70% by weight of the grout mixture, alternatively, from about 36% to about 64%.

In an embodiment, the clay component may comprise a benonite clay, for example, comprising one or more phyllosilicates. Such phyllosilicates may comprise montmorillonite, kaoliniate, halloysite, illite, vermiculite, talc, palygorskite, pyrophyllite, or combinations thereof. For example, in an embodiment, the bentonite clay may comprise sodium bentonite, calcium bentonite, aluminium bentonite, potassium bentonite, or combinations thereof. In an embodiment, the clay component may be present within the grout mixture in a range of from about 5% to about 20% by weight of the grout mixture, alternatively, from about 8% to about 18%.

In an embodiment, the fluid component may comprise a suitable aqueous fluid, alternatively, a substantially aqueous fluid (e.g., water, as disclosed herein). In an embodiment, a substantially aqueous fluid comprises less than about 50% of a nonaqueous component, alternatively less than about 45%, 40%, 35%, 30%, 25%, 20%, 15%, 10%, 5%, 4%, 3%, 2% or 1% of a nonaqueous component. Examples of suitable aqueous fluids include, but are not limited to, freshwater. In an embodiment, the fluid component may be present within the grout mixture in a range of from about 25% to about 50% by weight of the grout mixture, alternatively, from about 28% to about 46%.

In an embodiment, the grout mixture may further comprise one or more additives. Examples of such additives may include, but are not limited to thermal conductivity modifiers such as graphite (e.g., flaked graphite), polymers, crosslinkers, friction reducers, defoamers, foaming surfactants, fluid loss agents, weighting materials, latex emulsions, dispersants, vitrified shale and fillers, formation conditioning agents, density-adjusting materials such as hollow glass or ceramic beads, elastomers, carbon fibers, glass fibers, metal fibers, minerals fibers, of combinations thereof. One of skill in the art will appreciate that one or more of such additives may be added, alone or in combination, and in various suitable amounts to yield grout mixtures of a desired character and/or composition.

In an embodiment, providing the grout mixture may comprise mixing the sand component, the clay component, the fluid component, and, if present, the one or more additives so as to provide the grout mixture. The components may be mixed in any suitable order and/or fashion. For example, two or more components may be premixed to form a first mixture which may be later mixed with any additional components to yield the grout mixture. For example, the dry components (e.g., sand and clay) may be mixed to yield a dry pre-mixture which may be later mixed with the fluid component to yield the grout mixture. Additionally, in an embodiment all or a portion of the components may be mixed off-site to yield a premix and the premix later transported to the site of the geothermal installation. Additionally or alternatively, in an embodiment all or a portion of the components may be transported to or substantially proximate to the site of the geothermal installation and then mixed. The mixing may be performed utilizing an suitable type and/or configuration of machinery, for example, mixers, blenders, fluid delivery pumps, slurry pumps, conveyers, or combinations thereof. The components may be mixed for a suitable duration and at a suitable level of agitation, for example, to yield a substantially evenly mixed grout mixture.

In an embodiment, the method also comprises determining if the thermal conductivity of the grout mixture is within a predetermined range using a non-laboratory test 206. As used herein, the term "non-laboratory" test generally refers to a test which is not necessarily performed in a laboratory environment. As such, use of the term "non-laboratory" environment should not be construed as limiting the performance of any particular test or a portion thereof to any particular environment. Rather, the term "non-laboratory" test may be used to denote the capability to perform all or a portion of such test procedures outside of or away from what would be conventionally be recognized as a laboratory environment. In an embodiment, such a non-laboratory test may comprise any test conducted so that at least one test result may be produced and available within about 1 hour of initiation of such test procedures (for example, beginning upon sampling a grout mixture, as will be disclosed herein), alternatively, within about 2 hours, 4 hours, 6 hours, 8 hours, 10 hours, 12, hours, 15 hours, 18 hours, 1 day, or 1.5 days, or 2 days of initiation of the test procedures. In an embodiment, the non-laboratory test may comprise at least one test that may be conducted in a non-laboratory (e.g., a "field") environment. For example, in an embodiment the non-laboratory test may be conducted at the site of the heating and/or cooling system installation, or in substantially close proximity to the site of the heating and/or cooling system installation. For example, in an embodiment the non-laboratory test may be conducted within about 100 yards of an installation site, alternatively, within about ¼ mile of an installation site, alternatively, within about ½ mile of an installation site, alternatively, within 1 mile of an installation site, alternatively, within about 5 miles of an installation site, alternatively, within about 10 miles of an installation site, alternatively, within 15 miles of an installation site.

Figure 3:
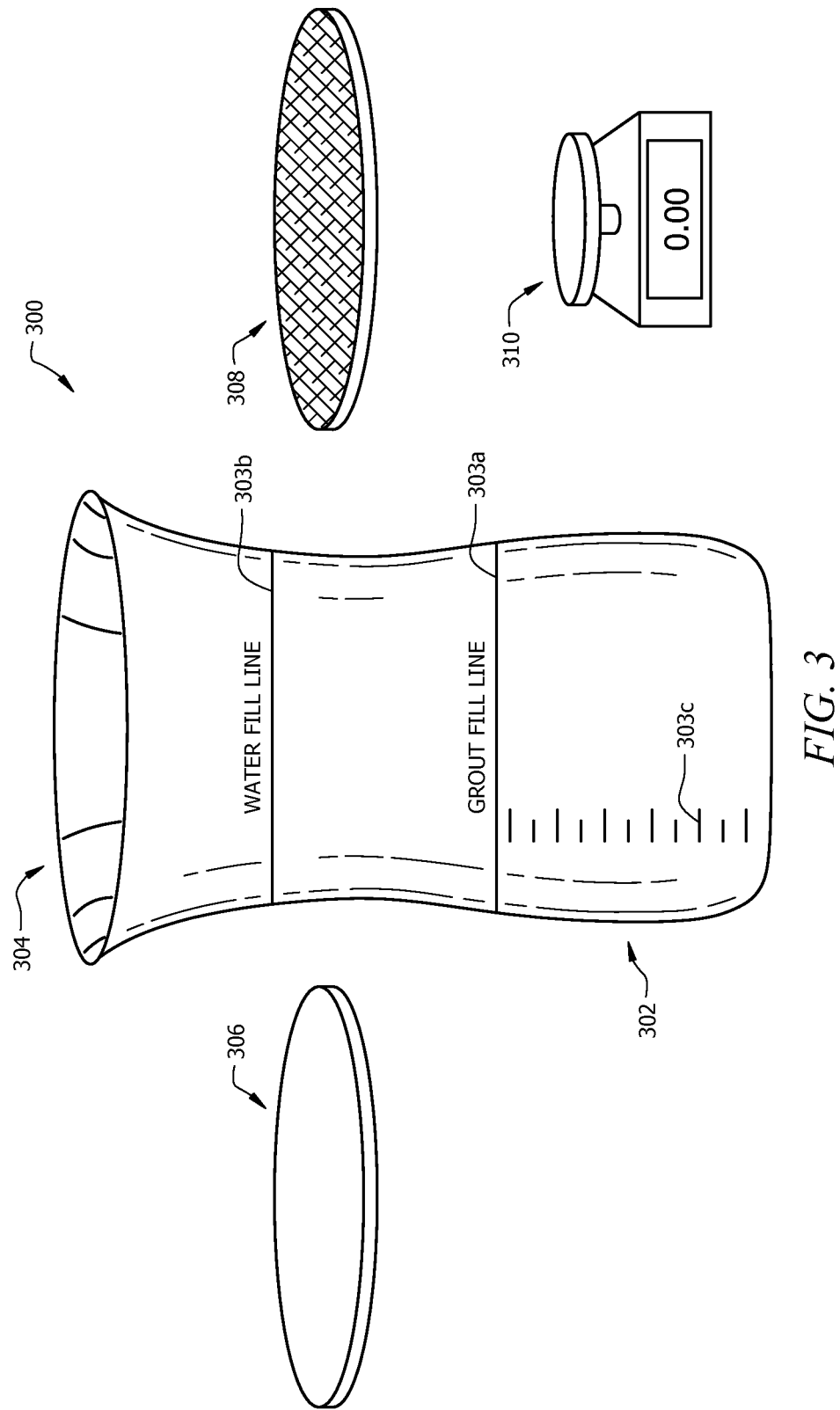
FIG. 3 is a schematic view of an embodiment of a thermal conductivity testing system according the present disclosure.

Referring to FIG. 3, an embodiment of a grout mixture thermal conductivity testing (TCT) system 300 is disclosed. In embodiments as will be disclosed herein, the TCT system 300 may be used in one or more of the steps of determining if the thermal conductivity of the grout mixture is within a predetermined range using a non-laboratory test 206 (e.g., sampling the grout mixture, performing the non-laboratory test to determine the thermal conductivity of the grout mixture, comparing the thermal conductivity of the grout mixture to a predetermined thermal conductivity threshold, or combinations thereof, as will also be disclosed herein). In the embodiment of FIG. 3, the TCT system 300 generally comprises a test container 302, a removable lid 306, and a separating member 308. In an additional embodiment, the TCT system 300 may further comprise a scale 310.

In an embodiment, the test container 302 may be generally configured to retain a given amount (e.g., volume or weight) of a sample of the grout mixture and a diluent, as will be disclosed herein. In an embodiment, the container may comprise a graduated cylinder or like container. For example, the graduated container may be configured to measure the amount (e.g., by weight or volume) of one or more materials disposed therein. For example, in the embodiment of FIG. 3 the test container 302 comprises at least one set of markings denoting various volumes within the test container 302, for example, absolute volumes and/or volumes as a percentage of another volume (e.g., relative to a total volume). Such markings may be set forth in any suitable metric or standardized (e.g., imperial) units. In an additional or alternative embodiment, the test container 302 may comprise a set of markings denoting the thermal conductivity of the grouting mixture disposed therein, as will be disclosed herein. In another additional or alternative embodiment, the test container 302 may comprise one or more "fill" lines denoting a fill volume and, optionally, a plurality of lines denoting the percentages of various volumes less than the "fill" volume, as will also be disclosed herein.

In an embodiment, the container may comprise any suitable material. Examples of such materials include, but are not limited to glass, plexi-glass, plastic, a phenolic material, metal, rubber, acrylic glass (e.g., poly(methyl methacrylate) or "PMMA"), a polycarbonate resin thermoplastic (e.g., Lexan®), or combinations thereof. In an embodiment, the material may be suitable for use in field conditions. For example, in an embodiment the test container 302 may comprise any suitable material characterized as resilient, for example, capable of withstanding significant forces and/or wear, for example, such that if the container is dropped on a hard surface, the container will not break and/or shatter. In an embodiment, the test container 302 may be characterized as transparent, alternatively, substantially transparent, alternatively, translucent. In an additional or alternative embodiment, the test container 302 may be substantially opaque, or opaque and further comprise a viewable portion (e.g., a transparent, substantially transparent, or translucent portion), such as a sight glass or a glass strip extending along the container 302.

In an embodiment, the test container 302 comprises at least one opening 304. In an embodiment, the at least one opening 304 may be configured to allow one or more materials (e.g., the grout mixture sample and/or diluent) to be disposed within the test container 302 and/or to allow materials to be removed therefrom. In the embodiment of FIG. 3, an opening 304 is disposed at one end of the test container 302 (e.g., the upper end). In an embodiment, the test container may comprise a plurality of openings like opening 304. For example in such an embodiment, a test container may comprise two openings, one at each of the respective ends thereof (e.g., the upper and lower ends).

In an embodiment, the removable lid 306 may be generally configured to sealingly and removably engage the at least one opening 304. In an embodiment, the removable lid 306 may comprise at least one ridge or lip configured to engage at least one complementary ridge disposed circumferentially around the at least one opening 304. In an embodiment, the complimentary ridges may be configured to be engaged and/or disengaged by rotating the lid 306 with respect to the opening 304 (e.g., a threaded or lug-slot quick connection). In another embodiment, the complimentary ridges may be engaged and/or disengaged by ratcheting at least one ridge over at least one other ridge. In still another embodiment, at least one ridge disposed on the lid 306 may snap over at least one ridge disposed around the opening 304. Alternatively, the removable lid 306 may be configured to be engaged and/or disengaged via a threaded interface. Suitable alternative couplings between the removable lid 306 and the opening 304 will be appreciated by one of skill in the art upon viewing this disclosure.

In an embodiment, the separating member 308 may be generally configured to separate various components of a grout mixture or other like slurry, for example, on the basis of size. For example, in an embodiment, the separating member 308 may be configured to separate substantially all of the sand present within a sample of a grout mixture or slurry from substantially all other components of the grout mixture. In an embodiment, the at least one separating member 308 may comprise mesh-like material, such as a screen, a fabric, or the like. In an embodiment, such a mesh-like material may generally comprise any suitable type or configuration thereof. Examples of suitable mesh-like materials may include, but are not limited to, synthetic fibers, metallic fibers, wires, natural fibers, the like, or combinations thereof.

In an embodiment, the mesh-like material may be characterized as having a suitable mesh size (e.g., a suitable opening size). As used herein, the term "mesh size" is used to refer to the sizing of a particular mesh material. Generally, mesh size may refer approximately to the greatest size of material (e.g., granular or particulate material) that will pass through a particular mesh size, for example, the nominal opening. The mesh size may also refer to the inside dimension of each opening in the mesh (e.g., the inside diameter of each square). For example, in an embodiment, the mesh-like material may be characterized as having a mesh size (e.g., openings) in the range of from about 70 microns to about 110 microns, alternatively, of from about 80 microns to about 100 microns, alternatively, of about 90 microns. In an additional or alternative embodiment, the mesh-like material may be characterized as having a mesh size of from about 150 mesh to about 270 mesh, alternatively, of from about 250 mesh to about 170 mesh, alternatively, of about 200 mesh, in accordance with the Tyler standardized mesh sizing. As will be appreciated by one of skill in the art upon viewing this disclosure, the sizing of the mesh-like material utilized may be varied to accommodate variously-sized components as may comprise the grout mixture.

In an embodiment, the separating member 308 is configured to seal around the opening 304. In an embodiment, the at least one separating member 308 may comprise at least one ridge that engages at least one complimentary ridge disposed around the at least one opening 304. In an embodiment, the complimentary ridges may engage and/or disengage by rotating the at least one separating member 308 around the at least one opening 304. In an embodiment, the complimentary ridges may engage and/or disengage by ratcheting at least one ridge over at least one other ridge. In an embodiment, at least one ridge disposed on the at least one separating member 308 may snap over at least one ridge disposed around the opening 304.

In an additional embodiment, multiple separating members like separating member 308 may be disposed over each other, for example, such that each of the separating members sealingly engage with the opening 304. In such an embodiment, multiple separating members 308 may have ridges that allow for sealing engagements around each separating member 308. In an embodiment, at least one separating member 308 may engage over at least one opening 304 and at least one lid member 306 may engage over the at least one separating member 308. In this embodiment, the at least one separating member 308 may seal around the opening 304.

Additionally, in this embodiment, the at least one lid 306 may seal around the opening and/or the at least one separating member 308. Thus, in this embodiment, the at least one lid member 306 may be removed from engagement with the opening 304, at least one separating member 308, and/or both the opening 304 and at least one separating member 308 without removing the at least one separating member 308 from engagement with the opening 304. That is, the lid 306 may fit over the separating member 308 and each may engage the opening 304 independently, for example, such that the lid can be removed while the separating member 308 remains in place.

In still another embodiment, the lid 306 and separating member 308 may comprise a single component. For example, in an embodiment the lid 306 and the separating member 308 may be independently hinged to the container 302, for example, such that the lid 306 and separating member 308 may be closed over the opening and secured, independently, into place. Alternatively, the lid 306 and the separating member 308 may be hinged to a collar, for example, which may be configured to engage (e.g., via a threaded or snap connection) the opening 304 of the test container 302.

In an embodiment where the TCT system 300 further comprises a scale 310, the scale 310 may be generally configured to measure the weight of the contents of the container 302. In an embodiment, the scale 310 may be configured to measure the weight of the grout mixture. In an embodiment, the scale 310 may be configured to measure the weight of the sand after the sand is separated from the grout slurry. In an embodiment, the scale 310 may be a digital scale, analog scale, and/or any similar device used to measure weight. The scale 310 may comprise a "Tare" function. Alternatively, the scale 310 may be calibrated for use with a particular container (e.g., test container 302), for example, such that the scale effectively reads "zero" when an empty test container 302 rests on the scale 310.

Figure 4:
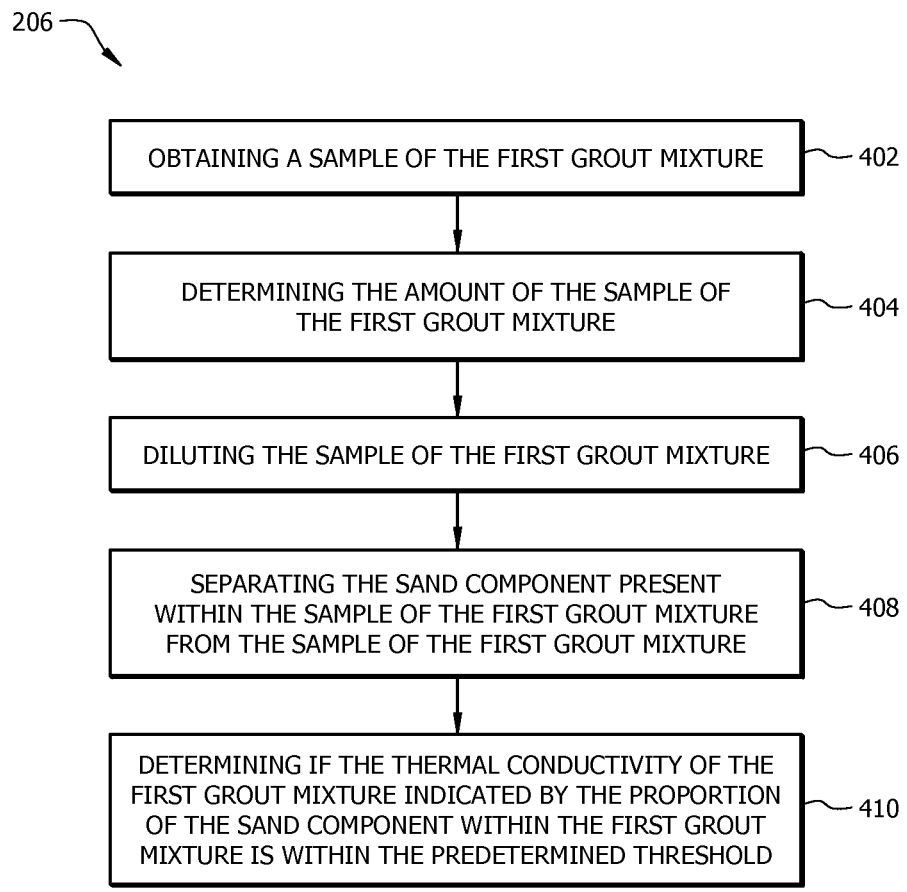
FIG. 4 is a block diagram of an embodiment of a method of determining if the thermal conductivity of a grout mixture is within a predetermined range using a non-laboratory test according to the present disclosure.

In an embodiment, determining if the thermal conductivity of the grout mixture is within a predetermined range using a non-laboratory test 206 may generally comprise obtaining a sample of (e.g., sampling) the grout mixture, performing a non-laboratory test to determine the thermal conductivity of the grout mixture, and comparing the thermal conductivity of the grout mixture to a predetermined thermal conductivity threshold, as will be disclosed herein. For example, referring to FIG. 4, an embodiment of a method for determining if the thermal conductivity of the grout mixture is within a predetermined range using a non-laboratory test 206 is illustrated. In the embodiment of FIG. 4, determining if the thermal conductivity of the grout mixture is within a predetermined range using a non-laboratory test 206 may generally comprise the steps of obtaining a sample of the grout mixture 402, determining the amount of the sample of the grout mixture 404, diluting the sample of the grout mixture 406, separating the sand component present within the sample of the grout mixture from the sample of the grout mixture 408, and determining if the thermal conductivity of the grout mixture indicated by the proportion of the sand component within the grout mixture is within the predetermined threshold 410, as will be disclosed herein. In one or more embodiments as will be disclosed herein, one or more of the steps of obtaining a sample of the grout mixture 402, determining the amount of the sample of the grout mixture 404, diluting the sample of the grout mixture 406, separating the sand component present within the sample of the grout mixture from the sample of the grout mixture 408, and determining if the thermal conductivity of the grout mixture indicated by the proportion of the sand component within the grout mixture is within the predetermined threshold 410 may be optional. For example, as will also be disclosed herein, two or more of the steps of obtaining a sample of the grout mixture 402, determining the amount of the sample of the grout mixture 404, diluting the sample of the grout mixture 406, separating the sand component present within the sample of the grout mixture from the sample of the grout mixture 408, and determining if the thermal conductivity of the grout mixture indicated by the proportion of the sand component within the grout mixture is within the predetermined threshold 410 may occur substantially contemporaneously.

In an embodiment, obtaining a sample of the grout mixture 402 may comprise taking, extracting, separating, or by any suitable means, otherwise obtaining a portion of the grout mixture, for example, after the grout mixture has been mixed as disclosed herein. In an embodiment, determining the amount of the sample of the grout mixture 404 may comprise determining the volume and/or the weight of the sample of the grout mixture. In an embodiment, obtaining a sample of the grout mixture 402 may occur substantially contemporaneously in time with determining the amount of the sample of the grout mixture 404. For example, in the embodiment where a TCT system, such as the TCT system 300, is utilized in one or more of the steps of determining if the thermal conductivity of the grout mixture is within a predetermined range using a non-laboratory test 206, sampling the grout mixture and/or determining the amount of the sample of the grout mixture may comprise placing an amount of the grout mixture within the test container 302. For example, as disclosed herein, the test container 302 may comprise one or more fill lines, denoting various volumes and/or relative volumes of the test container 302. In such an example, the volume of the sample of the grout mixture placed within the test container 302 may be sufficient to fill the test container to a first fill line (e.g., a "grout fill line," 303a). Alternatively, the volume of the sample of the grout mixture placed within the test container 302 may be sufficient to fill the test container to a given volume (e.g., as may be indicated by a volumetric scale one the test container 302). Alternatively, the weight of the grout mixture placed within the test container 302 may be determined, for example, using the scale 310, prior to placing the grout sample within the test container 302 or, alternatively, after placing the grout sample within the test container 302, for example, by taring (e.g., zeroing) the scale 310 with the test container 302 prior to disposing the grout sample therein. The amount (e.g., weight or volume) of the sample of the grout mixture may be recorded for later use. As such, in one or more or such embodiments, upon obtaining and placing a known or determined amount of the grout mixture within the test container 302 (e.g., the sample), such sample will have been obtained and its amount will have been known or determined.

In an embodiment, diluting the sample of the grout mixture 406 may comprise adding a diluent to the sample and agitating or otherwise mixing such that the diluent and the sample become sufficiently intermingled or dispersed. Examples of suitable diluents include, but are not limited to, water and other substantially aqueous fluids as disclosed herein. In an embodiment where a TCT system, such as the TCT system 300, is utilized in one or more of the steps of determining if the thermal conductivity of the grout mixture is within a predetermined range using a non-laboratory test 206, diluting the sample of the grout mixture may comprise placing an amount (e.g., a given volume or weight) of the diluent within the test container 302 with the sample of the grout mixture. In an embodiment, the amount (e.g., the volume or weight) of the diluent placed within the test container 302 may be known. For example and not intending to be bound by theory, in an embodiment the amount of diluent (e.g., water) may be sufficient to cause the clay component (e.g., bentonite) of the grout mixture to become over-hydrated, as will be disclosed herein. Alternatively, the amount of diluent is not necessarily known. For example, as noted above, in an embodiment the volume of the diluent placed within the test container 302 may be sufficient to fill the test container (along with the grout sample, which may already be present within the test container) to a second fill line (e.g., a "water fill line," 303b). In an alternative embodiment, the grout sample may be disposed within the test container after the diluent. That is the fill lines may be reversed, such that water may be added first, followed by the addition of grout.

In an embodiment, with the grout sample and the diluent disposed within the test container 302, the diluted grout sample may be agitated or mixed. For example, in an embodiment, agitating or mixing the diluted grout sample may comprise engaging the removable lid 306 with the opening 304 of the test container 302, for example, such that the test container is effectively sealed. In an embodiment, the separating member 308 is secured onto the opening 304, followed by the lid 306. With the test container sufficiently sealed, the test container 302 may be shaken for a suitable period of time to ensure that the contents (e.g., the diluted grout mixture) is substantially evenly distributed (e.g., thoroughly mixed). For example, the diluted grout mixture may be shaken (e.g., by hand or otherwise) for a duration of about 1 minute, alternatively, 2, 3, 4, 5, 6, 7, 8, 9, or 10 minutes, or for so long as is necessary. Alternatively, the diluted mixture may be mixed, stirred, blended, or otherwise agitated by any suitable method or apparatus, as may be recognized by one of skill in the art upon viewing this disclosure.

In an embodiment, separating the sand component present within the grout sample from the sample of the grout mixture 408 may comprise settling, filtering, centrifuging, or otherwise causing the sand within the sample to be separated from the remainder of the sample.

In an embodiment where a TCT system, such as the TCT system 300, is utilized in one or more of the steps of determining if the thermal conductivity of the grout mixture is within a predetermined range using a non-laboratory test 206, separating may comprise removing the removable lid 306 disposed over the opening 304 of the test container 302 and replacing it with the separating member 308. Alternatively, the separating member 308 may already be in place, for example, such that removal of the lid 306 exposes the separating member 308. In this embodiment, separating may also comprise turning the test container 302 (e.g., upside-down) so that diluted grout sample of the grout mixture may pass through the separating member 308. Alternatively, the separating member 308 may already be in place such that removal of the lid 306 exposes the separating member 308. In such an embodiment, as the dilute grout mixture passes out of the test container 302 via the separating member 308, substantially all of the sand component present within the grout sample may be retained by the separating member 308 and may remain in the test container 302, while substantially all of the remaining grout mixture passes through the separating member 308 and out of the test container 302. As noted above, the separating member 308, which comprises a mesh-like material, may be sized so as to retain substantially all of the sand within the grout sample while allowing substantially all other (e.g., fluid and/or particulate) materials to pass therethrough. Optionally, in an embodiment sand component (e.g., remaining within the test container 302) may be washed again, for example, by repeating the process of adding a diluent (e.g., water), agitating (e.g., shaking), and screening the sand component. In additional or alternative embodiments, separating may comprise similarly utilizing a filter or screen, a second container or the like, to similarly separate, for example, on the basis of size, the sand components of the grout mixture from substantially all other components of the grout mixture.

In an embodiment, determining if the thermal conductivity of the grout mixture indicated by the proportion of the sand component within the grout mixture is within the predetermined threshold 410 may comprise determining the amount of sand present within the sample grout mixture, determining the proportion of sand within the sample grout mixture, correlating the proportion of sand within the sample grout mixture to the thermal conductivity of the grout mixture, comparing the thermal conductivity to the predetermined thermal conductivity threshold, or combinations thereof. In an additional or alternative embodiment, determining if the thermal conductivity of the grout mixture indicated by the proportion of the sand component within the grout mixture is within the predetermined threshold 410 may comprise determining the amount of sand present within the sample grout mixture, determining the proportion of sand within the sample grout mixture, comparing the proportion of sand to a sand proportion threshold correlated to the predetermined thermal conductivity threshold, or combinations thereof.

For example, once the sand component has been separated from the other components of the sample grout mixture, the amount of the sand may be determined, for example, either on the basis of volume or on the basis of weight. For example, in an embodiment where the TCT system 300 is utilized, the amount of the sand component contained within the test container may be determined, for example, its volume, via the test container. As disclosed herein, in an embodiment the test container 302 may comprise markings or scales (e.g., lines 303c) indicating various volumes therein. Alternatively, in another embodiment, the amount of the sand component may be determined, for example, its weight, by weighing, for example, utilizing the scale 310.

In such an embodiment, where the amount (e.g., weight and/or volume) of the sand component present within the grout mixture sample has been so-determined, determining the proportion of the sand component within the sample grout mixture may comprise comparing the amount of the sand component (e.g., weight and/or volume) to the total amount of the sample grout mixture (e.g., weight and/or volume), for example, so as to calculate the proportion (e.g., percentage) of the sample which constitutes the sand component.

In an alternative embodiment, the proportion of the sand within the sample grout mixture may be determined directly. For example, as disclosed herein, in an embodiment the test container comprises markings denoting relative volumes therein. For example, the test container 302 may comprise one or more "fill lines" (e.g., a "grout fill line," 303a and a "water fill line," 303b) and a series of markings or scales 303c denoting relative volumes (e.g., proportions thereof). In an embodiment where the test container 302 has been filled to such a "grout fill line," 303a (e.g., with a given volume of the grout mixture) and substantially all other components have been removed from the test container 302, the amount of sand remaining therein (e.g., a volume of sand) will be indicative of the proportion of the sand component within the sample grout mixture. In such an embodiment, the markings or scale 303c may indicate a volumetric proportion (e.g., percentage) or the volume of the sand remaining within the test container 302. In such an embodiment, determining the proportion (e.g., on the basis of volume) of the sand component within the sample grout mixture may comprise reading such markings or scale 303c disposed on the test container 302.

In an embodiment where the proportion of the sand component within the sample grout mixture has been determined (e.g., on the basis of the sand component volume and/or weight), the thermal conductivity of the grout mixture may be determined based upon the proportion of the sand component within the grout mixture. For example, in an embodiment, a given proportion of the sand component within a grout mixture may correlate to a given thermal conductivity of that grout mixture. For example, in an embodiment a grout mixture having a sand component content in the proportion of from about of from about 50% to about 70% by either weight or volume may be expected to exhibit a thermal conductivity in the range of from about 0.69 Btu/hr.*Ft.*° F. to about 1.30 Btu/hr.*Ft.*° F., alternatively, a grout mixture having a sand component content in the proportion of from about of from about 55% to about 64% by either weight or volume may be expected to exhibit a thermal conductivity in the range of from about 0.85 Btu/hr.*Ft.*° F. to about 1.20 Btu/hr.*Ft.*° F.

In an alternative embodiment, the thermal conductivity of the grout mixture may be determined directly. For example, as disclosed herein, in an embodiment the test container comprises markings denoting various thermal conductivities as a function of relative volumes within the test container 302. For example, the test container 302 may comprise one or more "fill lines" (e.g., a "grout fill line," 303a and a "water fill line" 303b) and a series of markings or scales 303c denoting thermal conductivity as a function of each the respective relative volumes (e.g., proportions thereof). In an embodiment where the test container 302 has been filled to such a "grout fill line" (e.g., with a given volume of the grout mixture) and substantially all other components have been removed from the test container 302, the amount of sand remaining therein (e.g., a volume of sand) will be indicative of the thermal conductivity of the grout mixture. In such an embodiment, the markings or scale 303c may indicate a thermal conductivity based upon the volume of the sand component remaining. In such an embodiment, determining the thermal conductivity of the sample grout mixture may comprise reading such markings or scale 303c disposed on the test container 302 corresponding to the amount of sand therein.

In an embodiment, the thermal conductivity, for example, which may have been determined as disclosed herein, may be compared to a predetermined threshold, for example, to determine if the thermal conductivity of the grout mixture is within the predetermined threshold. In such an embodiment, the predetermined thermal conductivity threshold may be in the range of from 0.69 Btu/hr.*Ft.*° F. to about 1.20 Btu/hr.*Ft.*° F., alternatively, from about 0.88 Btu/hr.*Ft.*° F. to about 1.10 Btu/hr.*Ft.*° F. As will be appreciated by one of skill in the art upon viewing this disclosure, the thermal conductivity threshold may be any suitable range as may be desired, for example, as may be dependent upon the particular circumstances of a given operation.

In an alternative embodiment, the sand component proportion, for example, which may have been determined as disclosed herein, may be compared to a predetermined threshold for example, to determine if the sand content of the grout mixture is within the predetermined threshold. In this embodiment, the predetermined range may be in the range of from about 50% to about 70%, alternatively, from about 55% to about 64%. As noted above, a given proportion of the sand component within a grout mixture may correlate to a given thermal conductivity of that grout mixture. As will be appreciated by one of skill in the art upon viewing this disclosure, the sand component proportion threshold may be correlated to a desired thermal conductivity threshold, which may be any suitable range as may be desired, for example, as may be dependent upon the particular circumstances of a given operation.

Referring back to FIG. 2, in an embodiment, upon a finding that the thermal conductivity of the grout mixture is not within the predetermined range, the grout mixture may be altered. For example, in an embodiment where the thermal conductivity associated with the grout mixture is not within the predetermined or desired thermal conductivity range (e.g., as may be determined based upon the proportion of the sand component within the grout mixture, as disclosed herein), adjusting the grout mixture 208 may comprise adjusting the composition of the grout mixture (e.g. a first grout mixture) to yield an altered grout mixture (e.g. a second grout mixture), mixing or otherwise obtaining a new (i.e., second) grout mixture, or combinations thereof. For example, the composition of the grout mixture may be altered or adjusted by increasing or decreasing the relative amount of the sand component therein, increasing or decreasing the relative amount of the non-sand components therein, adding an additive (e.g., a thermal conductivity-improving additive, such as graphite), or combinations thereof.

In an embodiment, upon providing such an adjusted grout mixture, the process of determining if the thermal conductivity of the grout mixture (i.e., the adjusted mixture) is within a predetermined range using a non-laboratory test, for example, as has been disclosed herein, may be repeated. Additionally, such process may be repeat in as many iterations (e.g., with respect to a third, fourth, fifth, sixth, seventh, eighth, or other number of grout mixtures) as may be necessary or desired to develop a grout mixture having a desired thermal conductivity, for example, a thermal conductivity within the predetermined range.

In an embodiment, upon finding that the thermal conductivity of the grout mixture is within the predetermined range, the grout mixture may be utilized, for example, to secure the coil within a bore at the installation site. For example, in an embodiment where the thermal conductivity associated with the grout mixture is within the predetermined or desired thermal conductivity range (e.g., as may be determined based upon the proportion of the sand component within the grout mixture, as disclosed herein), securing the coil at the first location with the grout mixture 210 may comprise utilizing the grout mixture to place and secure the coils during the installation of a geothermal system. For example, in an embodiment, the grout may be pumped into the bores 124 at the first location so as to substantially surround and/or encase the coils 106 within the bores 124. Further, the grout mixture may be allowed to set up or harden within the bores 124.

In an additional embodiment where the thermal conductivity associated with the grout mixture is within the predetermined or desired thermal conductivity range, a second sample of the grout mixture may be taken. In such an embodiment, the second sample of the grout mixture may be obtained. In this embodiment, the second sample of the grout mixture may be tested, for example, in a laboratory or otherwise, to verify the results of field testing such as those obtained via the TCT system 300 to determine whether the grout mixture exhibits a thermal conductivity within the predetermined range.

In another additional embodiment, additional samples of the grout mixture may be subjected to non-laboratory testing, for example, as disclosed herein, for example, to improve the reliability of such determinations by carrying out multiple trials of such determinations.

In an embodiment, the methods, systems, and/or apparatuses disclosed herein may be advantageously employed in the performance of a grouting operation. For example, the methods, systems, and/or apparatuses disclosed herein may accelerate and/or improve the process of installing a geothermal heating and/or cooling system. Specifically, in an embodiment, these steps may allow for a field determination of the thermal conductivity of a grout mixture, thereby allowing work to continue without waiting for the performance of time-consuming laboratory tests. Therefore, in an embodiment, it is possible to utilize a grout slurry with greater assurance that is within the desired, predetermined range for thermal conductivity. In conventional embodiments, where no a field determination of the grout content of the grout mixture was possible, the installation of the geothermal heating and/or cooling system may be delayed for several days, for example, from about three days to perhaps more than about a week, while a sample of the grout mixture was sent to a laboratory to determine if the grout mixture was within the predetermined range.

Additionally, in an embodiment, if a field test determines that a sample of a grout mixture (e.g., a first grout mixture) is not within the predetermined range, a second grout mixture may be mixed almost immediately, for example, without needing to send a sample of the first grout mixture to the laboratory. Furthermore, in an embodiment, even if a sample of the grout mixture is sent to a laboratory for at least one test, the installation of the geothermal heating and/or cooling system may continue because of the assurances afforded by the field test. This feature may save substantial time, and therefore costs, associated with building and/or installing the geothermal heating and/or cooling system. For example, the installation of a geothermal heating and/or cooling system may continue substantially uninterrupted by laboratory testing verifying thermal conductivity coefficients of grout.

The exemplary chemicals, fluids, and/or additives disclosed herein may directly or indirectly affect one or more components or pieces of equipment associated with the preparation, delivery, recapture, recycling, reuse, and/or disposal of the disclosed chemicals, fluids, and/or additives. For example, the disclosed chemicals, fluids, and/or additives may directly or indirectly affect one or more mixers, related mixing equipment, mud pits, storage facilities or units, fluid separators, heat exchangers, sensors, gauges, pumps, compressors, and the like used generate, store, monitor, regulate, and/or recondition the exemplary chemicals, fluids, and/or additives. The disclosed chemicals, fluids, and/or additives may also directly or indirectly affect any transport or delivery equipment used to convey the chemicals, fluids, and/or additives to a well site or downhole such as, for example, any transport vessels, conduits, pipelines, trucks, tubulars, and/or pipes used to fluidically move the chemicals, fluids, and/or additives from one location to another, any pumps, compressors, or motors (e.g., topside or downhole) used to drive the chemicals, fluids, and/or additives into motion, any valves or related joints used to regulate the pressure or flow rate of the chemicals, fluids, and/or additives, and any sensors (i.e., pressure and temperature), gauges, and/or combinations thereof, and the like. The disclosed chemicals, fluids, and/or additives may also directly or indirectly affect the various downhole equipment and tools that may come into contact with the chemicals/fluids such as, but not limited to, drill string, coiled tubing, drill pipe, drill collars, mud motors, downhole motors and/or pumps, floats, MWD/LWD tools and related telemetry equipment, drill bits (including roller cone, PDC, natural diamond, hole openers, reamers, and coring bits), sensors or distributed sensors, downhole heat exchangers, valves and corresponding actuation devices, tool seals, packers and other wellbore isolation devices or components, and the like.

Additional Disclosure

The following are non-limiting, specific embodiments in accordance with the present disclosure:

A first embodiment, which is a subterranean grouting method comprising:

(a) placing a sample of a grout mixture within a test container;

(b) separating a sand component from the sample;

(c) determining if the grout mixture exhibits a thermal conductivity within a predetermined thermal conductivity range based upon a proportion of the sand component within the sample; and (d) upon determining that the grout mixture exhibits a thermal conductivity within the predetermined thermal conductivity range, securing a conduit within a subterranean bore with the grout mixture, wherein (a), (b), (c), and (d) are carried out proximate each other at a job site.

A second embodiment, which is the method of the first embodiment, further comprising, prior to separating the sand component of the sample, diluting the sample with a diluent added to the test container to yield a diluted sample.

A third embodiment, which is the method of the second embodiment, further comprising sealing the sample and the diluent within the test container; and shaking the test container to yield the diluted sample.

A fourth embodiment, which is the method of the third embodiment, wherein the test container is shaken by hand.

A fifth embodiment, which is the method of one of the third through the fourth embodiments, further comprising filtering the diluted sample to obtain the sand component within the test container.

A sixth embodiment, which is the method of the fifth embodiment, wherein the diluted sample is filtered by placing a screen or mesh material over an opening of the test container and allowing the diluted sample to pass through the screen or mesh material, wherein the screen or mesh material is sized such that the sand component remains within the test container and the remaining components of the diluted sample are removed from the container.

A seventh embodiment, which is the method of one of the first through the sixth embodiments, wherein the sand component remains within the test container upon separation from the grout mixture.

An eighth embodiment, which is the method of the seventh embodiment, wherein the thermal conductivity of the grout mixture is determined via one or more indicators on the test container corresponding to an amount of the sample in the test container, an amount of the sand component in the test container, or both.

A ninth embodiment, which is the method of the eighth embodiment, wherein the proportion of the sand component within the sample is determined by comparing the amount of the sand component to the amount of the sample to yield the proportion of the sand component on a volume or mass basis.

A tenth embodiment, which is the method of the eighth embodiment, wherein the amount of the sample in the test container corresponds to a first fill line on the container and the proportion of the sand component corresponds to one of a plurality of markings on the container below the first fill line.

An eleventh embodiment, which is the method of tenth embodiment, wherein the first fill line corresponds to a volume of the first sample and the plurality of markings on the container correspond to a volume of the sand component, wherein the proportion of the sand component within the sample is determined by comparing the volume of the sample with the volume of the sand component.

A twelfth embodiment, which is the method of one of the first through the eleventh embodiments, wherein (c) comprises:

(i) comparing the proportion of the sand component within the sample to a predetermined sand proportion threshold, wherein the predetermined sand proportion threshold is correlated to the predetermined thermal conductivity threshold;

(ii) comparing a sample thermal conductivity to the predetermined thermal conductivity threshold, wherein the sample thermal conductivity is correlated to the proportion of the sand component within the sample; or (iii) combinations thereof.

A thirteenth embodiment, which is the method of one of the first through the twelfth embodiments, wherein the proportion of the sand component within the sample is determined by:

(i) comparing a volume of the sand component to a volume of the first sample;

(ii) comparing a weight of the sand component to a weight of the first sample;

(iii) reading a series of markings indicating a volumetric proportion of a fill line on the test container; or (iv) combinations thereof.

A fourteenth embodiment, which is the method of one of the first through the thirteenth embodiments, wherein the proportion of the sand component within the sample is determined by weighing the sample and weighing the sand component.

A fifteenth embodiment, which is the method of one of the first through the fourteenth embodiments, wherein the test container comprises a first fill line corresponding to an amount of the sample placed in the test container, and wherein the series of markings below the first fill line indicate a volumetric proportion of the fill line.

A sixteenth embodiment, which is the method of one of the first through the fifteenth embodiments, wherein the test container comprises a first fill line corresponding to an amount of the sample placed in the test container, and wherein the series of markings below the first fill line indicate the sample thermal conductivity.

A seventeenth embodiment, which is the method of one of the first through the sixteenth embodiments, wherein the test container comprises a second fill line corresponding to an amount of diluent added to the test container, and wherein the second fill line is above the first fill line.

An eighteenth embodiment, which is the method of one of the first through the seventeenth embodiments, wherein the test container further comprises a lid coupled with a screen or mesh material.

A nineteenth embodiment, which is the method of one of the first through the eighteenth embodiments, further comprising:

upon determining that the grout mixture does not exhibit a thermal conductivity with the predetermined thermal conductivity range, adjusting the thermal conductivity of the grout mixture.

A twentieth embodiment, which is the method of the nineteenth embodiment, wherein adjusting the grout mixture comprises modifying the composition of the grout mixture, providing an alternative grout mixture, or combinations thereof.

A twenty-first embodiment, which is the method of one of the first through the twentieth embodiments, wherein the predetermined thermal conductivity range is from about 0.88 Btu/hr.*Ft.*° F. to about 1.20 Btu/hr.*Ft.*° F.

A twenty-second embodiment, which is a method for installing a geothermal heating and/or cooling system comprising:

disposing at least one flow conduit within a bore at a worksite;

providing a grout mixture;

sampling the grout mixture to yield a grout sample;

testing the grout sample using a non-laboratory test at the worksite to produce at least one test result;

determining if the at least one test result is within a predetermined range; and disposing the grout mixture proximate the flow conduit in the bore if the at least one test result is within the predetermined range.

A twenty-third embodiment, which is the method of the twenty second embodiment, further comprising sampling the grout mixture a second time and sending a second sample associated with the second sampling to a laboratory for verification of the at least one test result is within a predetermined range.

A twenty-fourth embodiment, which is the method of one of the twenty-second through the twenty-third embodiments, the method further comprising adjusting the grout mixture to create an adjusted grout mixture if the at least one test result is not within the predetermined range.

A twenty-fifth embodiment, which is the method of the twenty-fourth embodiment, the method further comprising:
 providing an adjusted grout mixture;
 sampling the adjusted grout mixture;
 testing a grout sample of the adjusted grout mixture using a non-laboratory test at the worksite to produce at least one test result;
 determining if at least one test result is within a predetermined range; and
 disposing the adjusted grout mixture proximate the flow conduit in the bore if the at least one test result is within the predetermined range.

A twenty-sixth embodiment, which is the method of the twenty-fifth embodiment, the method further comprising sampling the new grout mixture a second time and sending a second sample associated with the second sampling to a laboratory for verification testing if the at least one test result is within a predetermined range.

A twenty-seventh embodiment, which is the method of one of the twenty-second through the twenty-sixth embodiments, wherein providing a grout mixture comprises mixing at least one type of sand with at least binder material such as cement.

A twenty-eighth embodiment, which is the method of one of the twenty-second through the twenty-seventh embodiments, wherein sampling the grout mixture comprises extracting a portion of the grout mixture to obtain a sample of the grout mixture.

A twenty-ninth embodiment, which is the method of one of the twenty-second through the twenty-eighth embodiments, wherein the non-laboratory test comprises any test conducted so that at least one test result may be produced within a day of conducting the test.

A thirtieth embodiment, which is the method of one of the twenty-second through the twenty-ninth embodiments, wherein the predetermined range is a range of thermal conductivity coefficients.

A thirty-first embodiment, which is the method of the thirtieth embodiment, wherein the range of thermal conductivity coefficients is between about 0.85 Btu/hr.*Ft.*° F. and about 1.35 Btu/hr.*Ft.*° F.

A thirty-second embodiment, which is the method of one of the twenty-second through the thirty-first embodiments, wherein the predetermined range is a range of percentage of sand by volume of the grout mixture.

A thirty-third embodiment, which is the method of one of the twenty-second through the thirty-second embodiments, wherein the percentage of sand by volume of the grout mixture is between about 50% and about 70%.

A thirty fourth embodiment, which is the method of one of the twenty-second through the thirty-third embodiments, wherein the predetermined range is a range of percentage of sand by weight of the grout mixture.

A thirty-fifth embodiment, which is the method of the thirty-fourth embodiment, wherein the percentage of sand by weight of the grout mixture is between about 50% and about 70%.

A thirty-sixth embodiment, which is a method of testing a grout mixture using a non-laboratory test comprising:
 disposing a sample of a grout mixture into a container proximate a jobsite;
 measuring the sample of the grout mixture;
 diluting the sample of the grout mixture using at least one fluid added to the container;
 agitating the sample of the grout mixture within the container by hand;
 separating sand from the sample of the grout mixture, wherein the sand remains in the container; and
 producing at least one test result.

A thirty-seventh embodiment, which is the method of the thirty-sixth embodiment, wherein measuring comprises measuring the weight of the sample of the grout mixture.

A thirty-eighth embodiment, which is the method of one of the thirty-sixth through the thirty-seventh embodiments, wherein diluting comprises adding a sufficient quantity of fluid to form a grout slurry.

A thirty-ninth embodiment, which is the method of one of the thirty-sixth through the thirty-eight embodiments, wherein agitating comprises blending the sample of the grout mixture.

A fortieth embodiment, which is the method of one of the thirty-sixth through the thirty-ninth embodiments, wherein the at least one test result comprises a thermal conductivity coefficient associated with the grout mixture determined from the amount of sand remaining in the container.

At least one embodiment is disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting features of the embodiment(s) are also within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, $R_l$, and an upper limit, $R_u$, is disclosed, any number falling within the range is specifically disclosed. In particular, the following numbers within the range are specifically disclosed: $R=R_l+k*(R_u-R_l)$, wherein k is a variable ranging from 1 percent to 100 percent with a 1 percent increment, i.e., k is 1 percent, 2 percent, 3 percent, 4 percent, 5 percent, . . . , 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim means that the element is required, or alternatively, the element is not required, both alternatives being within the scope of the claim. Use of broader terms such as comprises, includes, and having should be understood to provide support for narrower terms such as consisting of, consisting essentially of, and comprised substantially of. Accordingly, the scope of protection is not limited by the description set out above but is defined by the claims that follow, that scope including all equivalents of the subject matter of the claims.

Each and every claim is incorporated as further disclosure into the specification and the claims are embodiment(s) of the present invention.

What is claimed is:

1. A. subterranean grouting method comprising:
   (a) placing a sample of a gout mixture within a test container;
   (b) separating a sand component from the sample;
   (c) determining if the grout mixture exhibits a thermal conductivity within a predetermined thermal conductivity v range based upon to proportion of the sand component within the sample; and
   (d) upon determining that the grout mixture exhibits a thermal conductivity within the predetermined thermal conductivity maw, seeming a conduit within a subterranean bore with the grout mixture,
   wherein (a), (b), (c), and (d) are carried out proximate each other at a job site.

2. The method of claim 1, further comprising prior to separating the sand component of the sample, diluting the sample with a diluent added to the test container to yield a diluted sample.

3. The method of claim 2, further comprising sealing the sample and the diluent within the test container; and shaking the test container to yield the diluted sample.

4. The method of claim 3, wherein the test container is shaken by hand.

5. The method of claim 3, further comprising filtering the diluted sample to obtain the sand component within :the test container.

6. The method of claim 5, wherein the diluted sample is filtered by placing a screen Or mesh material over an opening of the test container and allowing the diluted sample to pass trough the screen or mesh material, wherein the screen or mesh material is sized such that the sand component remains within the test container and remaining components of the diluted sample are removed from the test container.

7. The method of claim 1, wherein the sand component remains within the test container upon separation from the grout mixture.

8. The method of claim 7, wherein the thermal conductivity of the grout mixture is determined via one or more indicators on the test container corresponding to an amount of the sample in the test container, an amount of the sand component in the test container, or both.

9. The method of claim 8, wherein the proportion of the sand component within the sample is determined by corn paring the amount of the sand component to the amount of the sample to yield the proportion of the sand component on a volume or mass basis.

10. The method of claim 8, wherein the amount of the sample in the test container corresponds to a first fill line on the container and the proportion of the sand component corresponds to one of a plurality of markings on the container below the first fill line.

11. The method of claim 10, wherein the first fill line corresponds to a volume of the sample and the plurality of markings on the container correspond to a vaunt of the sand component, wherein the proportion of the sand component within the sample is determined by comparing the volume of the sample with the volume of the sand component.

12. The method of claim 1, wherein (c) comprises:
   (i) comparing the proportion of the saner component within the sample to a predetermined sand proportion range, wherein the predetermined sand proportion range is correlated to the predetermined thermal conductivity range;
   (ii) comparing a sample thermal conductivity to the predetermined thermal conductivity range, wherein the sample thermal conductivity is correlated to the proportion of the sand component within the sample; or
   (iii) combinations thereof.

13. The method of claim 1, wherein the proportion of the sand component within the sample is determined by:
   (i) comparing a volume of the sand component to a volume of the sample;
   (ii) comparing a weight of the sand component to a weight of the sample;
   (iii) reading a series of markings indicating a volumetric proportion of a fill line on the test container; or
   (iv) combinations thereof.

14. The method of claim 1, wherein the proportion of the sand component within the sample is determined by weighing the sample and weighing the sand component.

15. The method of claim 1, wherein the test container comprises a first fill line corresponding to an amount of the sample placed in the test container, and wherein the series of markings below the first fill line indicate a volumetric proportion of the fill line.

16. The method of claim 1, wherein the test container comprises a first fill line corresponding to an amount of the sample placed in the test container, and wherein the series of markings below the first fill line indicate the sample thermal conductivity.

17. The method of claim 1, wherein the test container comprises a second fill line corresponding to an amount of diluent added to the test container, and wherein the second fill line is above the first fill line.

18. The method of claim wherein the test container further comprises a lid.

19. The method of clam 1, further comprising:
   upon determining that the grout mixture does not exhibit a thermal conductivity with the predetermined thermal conductivity range, adjusting the thermal conductivity of the grout mixture.

20. The method of claim 19, wherein adjusting tine grout mixture comprises modifying the composition of the grout mixture, providing an alternative grout mixture, or combinations thereof.

21. The method of claim 1, wherein the predetermined thermal conductivity range is from about 0.88 Btu/hr.*Ft.*° F. to about 1.20 Btu/hr.*Ft.*° F.

* * * * *

UNITED STATES PATENT AND TRADEMARK OFFICE
CERTIFICATE OF CORRECTION

PATENT NO. : 8,851,746 B2
APPLICATION NO. : 13/661744
DATED : October 7, 2014
INVENTOR(S) : Ryan Patrick Collins et al.

Page 1 of 1

It is certified that error appears in the above-identified patent and that said Letters Patent is hereby corrected as shown below:

In the Claims:

Column 21, Claim 1, line 11, replace "v range based" with --range based--.

Column 21, Claim 1, line 15, replace "conductivity maw, seeming" with --conductivity range, securing--.

Column 21, Claim 5, line 29, replace "within :the" with --within the--.

Column 21, Claim 6, line 32, replace "Or mesh" with --or mesh--.

Column 21, Claim 6, line 34, replace "trough" with --through--.

Column 21, Claim 9, lines 47-48, replace "com paring" with --comparing--.

Column 21, Claim 11, line 58, replace "vaunt" with --volume--.

Column 22, Claim 12, line 5, replace "saner" with --sand--.

Column 22, Claim 18, line 43, replace "claim wherein" with --claim 1 wherein--.

Column 22, Claim 20, line 50, replace "tine" with --the--.

Signed and Sealed this
Twenty-third Day of December, 2014

Michelle K. Lee
*Deputy Director of the United States Patent and Trademark Office*